United States Patent [19]

De Ferra et al.

[11] Patent Number: 5,700,668
[45] Date of Patent: Dec. 23, 1997

[54] PROCESS FOR THE INDUSTRIAL PREPARATION OF PHOSPHATIDYLSERINE

[75] Inventors: Lorenzo De Ferra; Pietro Massardo; Oreste Piccolo; Stefano Servi, all of Patrica, Italy

[73] Assignee: Italfarmaco Sud S.p.A., Patrica, Italy

[21] Appl. No.: 570,000

[22] Filed: Dec. 8, 1995

[51] Int. Cl.$^6$ ............................ C12N 1/20; C12P 13/04
[52] U.S. Cl. .................. 435/106; 435/116; 435/253.5; 435/886
[58] Field of Search .................. 435/106, 116, 435/253.5, 886

[56] References Cited

U.S. PATENT DOCUMENTS 5,084,215  1/1992  Kearns et al. ........................ 554/19

OTHER PUBLICATIONS

APS Abstract Yamane et al JP02–7990 Mar. 20, 1990.

*Primary Examiner*—Herbert J. Lilling
*Attorney, Agent, or Firm*—Griffin, Butler, Whisenhunt & Kurtossy

[57] ABSTRACT

The invention relates to a process for the preparation of phosphatidylserines by reacting racemic or enantiomerically pure serine, preferably (L)-serine, with natural phosphatides, such as soybean or egg lecithin, or with synthetic phosphatides, in the presence of a phospholipase D, having transphosphatidylating activity, in an aqueous/organic diphasic system.

16 Claims, No Drawings

PROCESS FOR THE INDUSTRIAL PREPARATION OF PHOSPHATIDYLSERINE

The present invention relates to a process for the preparation of phosphatidylserines of formula (I), hereinafter referred to as PS, by reacting racemic or enantiomerically pure serine, preferably (L)-serine, with natural phosphatides, such as soybean or egg lecithin, or with synthetic phosphatides of formula (II), in the presence of a phospholipase D, hereinafter referred to as PLD, having transphosphatidylating activity, in an aqueous/organic dipbasic system.

The compounds of the invention have the general formulae (I) and (II):

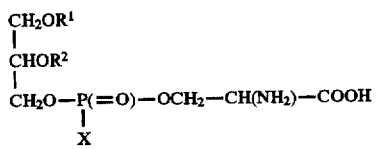

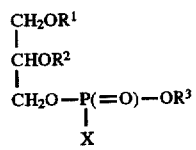

wherein $R^1$ and $R^2$ which are the same or different are a $C_{10}$–$C_{30}$ acyl optionally mono- or polyunsaturated; X=OH or OM, wherein M is an alkali, alkaline-earth metal, ammonium or alkylammonium (inner salt included); $R^3$=$CH_2CH_2NH_2$ or $CH_2CH_2\ N^+(CH_3)_3$.

The importance of the compounds (I) is various, particularly in the preparation of pharmaceutical compositions for the therapy of involutive cerebral syndromes of different origin, such as vascular pathologies on atheroschlerotic base or not and/or senile decline; for the preparation of liposomial formulations and more recently for dietetic compositions comprising natural lecithins, particularly soy lecithin enriched in phosphatidyl-L-serine, hereinafter referred to as PS(L), containing polyunsaturated fatty acids as acyl residues.

The increasing demand for industrial amounts of PS(L) at a reasonable cost prompted the Applicant to carry out a thorough investigation to fulfill such a need.

BACKGROUND OF THE INVENTION

The preparation of phosphatides (I) by means of PLD as enzymatic catalyst in the transphosphatidylation reaction, is already known. However, the known procedures relate to the laboratory scale preparation (small number of grams), and they suffer from a series of drawbacks, hereinafter specified, hindering their industrial scaling-up.

It also known that the industrial reproducibility of laboratory procedures of enzymatic reactions, especially when crude enzymes are used, is not easily accomplished.

It is moreover important to mention that PLD enzymes are able to catalyze the aqueous hydrolysis of phosphatides to give phosphatidic acid, hereinafter referred to as PA, in competition with the transphosphatidylation reaction, the kinetics of the two reactions being highly affected by the reaction conditions and by the origin of said enzyme.

For instance, Comfurius P. et al. Biochim. Biophys. Acta 488, 36 (1977) first discloses the production of an about 1/1 mixture of PS(L) and PA, by reacting under pressure at 45° C. and at pH 5.6, in a diphasic ethyl ether/water system, egg lecithin or synthetic phosphatidylcholines with L-serine in the presence of partially purified PLD enzyme (from cabbage).

PS(L) is then purified by chromatography on cellulose using a chloroform/methanol mixture as eluent. It is evident that such a procedure is not suited to an industrial production both due to the use of ethyl ether and the low selectivity.

More interesting results have been reported by Yamane T. et al. Biochim. Biophys. Acta 1003, 277 (1989) wherein PLD enzymes of different origin (from cabbage and from Streptomyces strains) having different transphosphatidylating activities in the PC conversion with (D)- and (L)-serine, were compared a study of the different reaction parameters such as pH, solvent, temperature, reagents and enzyme (studied also after immobilization) concentrations, was also carried out.

The considered pH ranged from 5.5 to 7.0, the most effective dipbasic solvent system for the free enzyme being ethyl ether-water or ethyl acetate-water, whereas solvents such as benzene, toluene and chloroform are less effective; moreover ethyl acetate is not suitable to the immobilized enzyme. Temperature ranges from 20° C. to 40° C. and the tests were preferably carried out at 30° C. even though the reaction rate increases with the temperature; the tests were carried out at a 3.4M serine concentration which corresponds to its solubility at pH 5.6 at 30° C., whereas the PC concentration is kept very low (<53.4 mM, usually 17.8 mM) and the enzyme concentration is 0.2–0.8 U/ml (a unit is defined as the enzyme amount which hydrolyzes in one min 1 μmol pure PC to PA at 30°±0.5° C.).

Using a highly purified phosphatidylcholine, hereinafter referred to as PC, an almost complete conversion of PS would be obtained in the optimum reaction conditions. Differently from PLD from cabbage, bacterial PLDs similarly catalyze transphosphatidylation with (D) and (L)-serine.

Notwithstanding the advantages with respect to the previously used method, even this process cannot be considered to be industrially applicable since the study was aimed at finding the optimum conditions using purified enzymes and highly pure PC, whereas nothing is said about the use of low cost and low purity lecithins and the use of non-purified enzymes for industrial purposes.

JP-A-63 036,791 discloses the use of activated charcoal or other carriers in large amounts as adsorber for serine and PLD, suspending said material in a low water content (preferably<0.2%) solvent wherein the phospholipid is dissolved, so as to decrease the competitive formation of PA. Alternatively said carrier is loaded onto a column and the organic solvent is eluted through the column. This process is difficult to apply industrially since the enzyme and the substrate should be entrapped on the same carrier and a low water content is requested.

JP-B-63 036,792 discloses the use of cabbage PLD in a water/diisopropyl ether diphasic system as the solvent, operating in micellar conditions. A very low conversion is obtained from a partially purified soy lecithin, having a PC content of about 68%, the PS(L) content at the end of the reaction being 24%.

Better results were reported in JP-B-02 079,996, wherein a Streptomyces PLD in ethyl acetate is used; however, even using a synthetic, pure phosphatidyl-choline as the starting material, the yield in the corresponding PS(L) is about 68%, similarly to that reported in JP-B-63 123,389, wherein an egg PC in ethyl ether was converted into PS(D) by means of a Nocardiopsis or Actinomadura PLD.

Finally, Okahata Y. et al. J. Chem. Soc. Perkin trans. 1, 919 (1995) disclose the use of Streptomyces PLD coated with lipids, prepared separately, which are able to exert catalytic activity in an organic solvent at pH 5.5. This enzyme should be much more active than the crude enzyme with which the reaction is often not complete. In spite of the notation in the article that the maximum reaction rate of the crude enzyme is achieved at more acidic pH values of about 4, the reaction rate is however<2% of that of lipid-coated enzyme.

Using a diphasic water/benzene system as the solvent, egg PC at 40° C. in 24 h with the lipid coated enzyme, a PS(L) in an about 75% yield would be obtained.

From the teachings of the above discussed prior-art, those skilled in the art would conclude that:
- the use of crude lecithins is not convenient or even possible;
- the use of a purified or at least not crude and therefore expensive enzyme is necessary;
- the industrially acceptable, non-toxic, environmentally compatible solvents are difficult to use;
- a remarkable serine excess is necessary, therefore involving the need for recovering or recycling serine. Moreover the chromatographic procedures disclosed in the above methods are further grounds against the industrial applicability of said methods.

SUMMARY OF THE INVENTION

Surprisingly, the present invention provides a process which overcomes the prior-art drawbacks and disadvantages using fermentation broths of microorganisms strains producers of extracellular PLD, optionally dialyzed through membranes with a suitable cut-off, in a diphasic water/organic solvent system, preferably water/toluene.

The invention provides therefore a process for the preparation of compounds (I) comprising the reaction of phosphatides (II) with racemic or enantiomerically pure serine, preferably with L-serine, in the presence of crude phospholipase D from centrifuged fermentation broths of microorganisms strains producing extracellular PLD having high transphosphatidylation activity.

The invention, in a further embodiment, also provides a new Streptomyces sp. strain producing an extracellular PLD having high transphosphatidylating activity.

The strain has been deposited at ATCC on 13.10.1995, under accession number 55717.

The process of the invention can be effectively carried out also with suitable known strains.

DESCRIPTION OF THE PREFERRED EMBODIMENTS

The preferred organic solvent, toluene, provides a number of advantages such as low cost, low toxicity, environmental compatibility, high solubility of phosphatide (II) and particularly of crude lecithins and of PS, low solubility of serine, allowing the removal and recovery of this amino acid, present in large excess, from the produced PS; compatibility with the enzymatic activity of PLD and affording a sufficiently fast and highly selective (PS to PA ratio) transphophatidylation reaction.

Toluene moreover allows, through repeated solubilizations and concentrations, complete removal from the used lecithin of the primary alcohols, particularly ethanol, which are present up to 0.5% in commercial lecithin. These alcohols are extremely reactive as serine competitors in the transphosphatidylation reaction and could yield undesired phosphatides, such as phosphatidylethanol, up to 8% with a consequent decrease in PS quality and yield.

The reaction is preferably carried out at 25°±5° C. at pH values ranging from 4 to 4.5, whereas in the prior art methods the pH was above 5. Furthermore, in contrast with previously reported results, we have observed a decreased selectivity when the reaction temperature was ≦40° C. The other reaction conditions, such as stirring and addition procedures, as well as the presence of additives such as alkaline or alkali-earth metal ions, are conventional and may be easily determined by those skilled in the art.

Surprisingly, the process of the invention may be advantageously applied both to high purity lecithins such as Epikuron 200(R) (95% soy PC, available from Lucas Meyer) and to low-cost, low purity lecithins such as Epikuron$^{(R)}$135 (Lucas Meyer) which consists of a mixture of PC (35%) and PE (8%) and triglycerides (50%); the same applies for egg PC such as Ovothin 160 (60% egg PC, Lucas Meyer) or synthetic phosphatides of formula (II).

Purification of the obtained PS, relies on the different partition coefficients in diphasic organic solvent systems of phosphatides such as PS, PA, PC, PE and the corresponding lysophosphatides in the form of the corresponding salts, particularly the corresponding calcium salts in the diphasic heptane/methanol system.

It is possible to increase, in a 90% yield, the purity of a PS(L) obtained from Epikuron 200 from 88% to 95% thanks to its preferential bipartition in the heptane phase; similarly, the purity of a PS(L) obtained from Epikuron 135 was increased from 58% to about 80%. A further purification of PS can be obtained by crystallization from heptane/acetone in the form of the calcium salt and subsequent conversion into any other salt, according to conventional techniques.

Serine may be recovered according to different methods. A first method comprises the partial concentration under reduced pressure of the aqueous solution from the transphosphatidylation reaction, after separation of the toluene phase and after treatment with activated charcoal, and the crystallization of serine from said solution. Alternatively, it is possible to recycle the aqueous phase from the completed reaction in a subsequent batch, avoiding the isolation of the contained serine. This is carried out by treating the aqueous phase with activated charcoal, removing inorganic and choline salts by electrodialysis at pH 5.7, which is the serine isoelectric pH, in a tangential flow electrodialysis apparatus, keeping the pH value constant during the electrodialysis; the resulting aqueous solution may be used as such or after optional concentration of the aqueous solution under vacuum or by reverse osmosis.

A similar process may also be carried out using, instead of electrodialysis, ion-exchange resins to remove inorganic and choline salts and then concentrating the aqueous solution with the above mentioned procedures.

The process of the invention can be conveniently applied to the preparation of phosphatidyl-(L)-serines wherein $R^1$ and $R^2$ are acyl chains of palmitic, stearic, oleic, linoleic acids in similar proportions to that of soy lecithin or wherein $R^1$ and $R^2$ are acyl chains of palmitic, stearic, palmitoleic, oleic, linoleic, arachidonic acids in similar proportions to that of egg lecithin.

The procedures reported in the following further exemplify the invention.

EXAMPLE 1

Preparation of the PLD catalyst. General procedure.

The different strains of Streptomyces used were grown under stirring for 24 h in 1 l flasks containing 200 ml of a medium consisting of glucose (10 g/l), yeast extract (20 g/l), peptone (5 g/l), $K_2HPO_4$ (2 g/l), $MgSO_4$ heptahydrate (0.5 g/l), at pH 7 by addition of 1M HCl. The cultures were used to inoculate 10 l fermenters containing 5 l of the same nutrient medium, and an anti-foam agent if necessary, and fermentation was continued for 24 h at 30° C., under air stream with stirring at 500 rpm, keeping a constant pH value of 7 by automatic addition of 0.1M NaOH or of 0.1M HCl. At the end, the broth was centrifuged and stored at 4° C.

The industrial fermentation was carried out with similar procedures in a 2,000 l reactor, reaching after 23 h a final activity of the broth of 2-3 Ku/l of PLD, determined by the test described in literature [Biotechn. Techn., 7, 795 (1993)]. The resulting fermentation broth was centrifuged and used as such or after concentration to about 1/10 of the starting volume, at a pH buffered to a value of 5.6 using of 0.1M sodium acetate, by ultrafiltration through Millipore membranes having a cut-off of 10000 Dalton.

EXAMPLE 2

Preparation of PS(L) starting from soy lecithin Epikuron 200

20 g of Epikuron 200 (Lucas Meyer) and 100 ml of toluene are placed into a 1,000 ml reactor, under nitrogen, and the solution is concentrated under vacuum distilling about 80 ml of the solvent. Fresh toluene is added and the solution is concentrated again under reduced pressure. The procedure is repeated until reaching a content in ethanol or other $C_1-C_4$ alcohols, which are usually present in commercial lecithin, below 20 ppm. The residue is mixed into fresh toluene to a volume of 400 ml and 94.5 g of (L)-serine is added. The resulting suspension is mixed with the aqueous solution (300 ml) containing PLD from ATCC 55717, prepared according to the procedures of example 1 and having an enzymatic activity of 2 U/ml. Thereafter is added at 10° C. 3.34 g of calcium chloride, 4.08 g of sodium acetate trihydrate and about 3 g of glacial acetic acid to obtain a pH around 4.5. The resulting diphasic system is heated to a temperature of 25°±2° C. and kept under strong stirring for about 6h. The mixture is then filtered on decalite, which is further washed with 2×100 ml of toluene; the organic phase is separated from the aqueous phase containing the serine excess, and concentrated under reduced pressure to give a residue (22.3 g) which is taken up into 525 ml of n-heptane and 171 ml of methanol. The lower methanol phase is discarded whereas the higher one is further extracted with 220 ml of methanol. After separation, the higher phase is concentrated under vacuum to small volume, added, under stirring at −5° C., to 400 ml of acetone, filtered and dried under vacuum to give 15 g of PS(L) calcium salt with a 97% HPLC (PA content <3%).

The aqueous phase containing serine is treated with 16 g of activated charcoal and filtered on decalite; subsequently it is concentrated under vacuum (30 mm Hg) distilling off about 70% of the solvent, then cooled, filtered and dried at 50° C, to give about 52 g of pure (L)-serine. Mother liquors containing the excess of serine (about 43 g) are added to the aqueous phase derived from a further PS synthesis for a subsequent recovery.

EXAMPLE 3

Preparation of PS(L) starting from soy lecithin Epikuron 135

400 Kg of Epikuron 135 (Lucas Meyer), 3000 l of toluene, 100 l of water are placed into a 5,000 l stainless steel reactor, under nitrogen, and the mixture is concentrated under vacuum, distilling at 45° C. about 1,000 l of solvents. Another 6,000 l stainless steel reactor is loaded with 1,355 l of fermentation broth from ATCC 55717, containing about 3 KU/l of PLD, 22.7 kg of calcium chloride, 27.6 kg of sodium acetate trihydrate, and at 10° C. 22 l of 80% acetic acid 625 kg of L-serine (final pH 4.2). The two solutions are combined and the resulting mixture is heated to and kept at 25° C. with strong stirring for 8 h. HPLC analysis shows a PS(L) content of about 75% of the total phospholipids. The mixture is then added to a suspension of 36 kg of decalite in 500 l of toluene and filtered, washing the filter with 400 l of toluene/water (3/1, V/V). The aqueous phase is then separated and treated to recover (L)-serine analogously to that described in the subsequent example 6, whereas the organic phase, after further filtration on decalite, is concentrated under vacuum to an about 440 kg residue, which is added to 5,000 l of acetone and stirred for about 6 h at room temperature. After cooling the mixture to 0° C., the product is filtered to give about 323 kg of PS(L) humid calcium salt (50%).

The product is further purified by treatment with 2,000 l of acetone and dried, to give about 273 kg of PS(L) calcium salt (58%).

A 20 g sample was purified by extraction with heptane/methanol, analogously to that described in example 2, give 11,6 g of PS(L) calcium salt (80%).

EXAMPLE 4

Preparation of PS(L) starting from egg lecithin.

13 g of Ovothin 160 (60% PC; Lucas Meyer), 158 ml of toluene and 38 g of (L)-serine are placed into a 500 ml reactor, under nitrogen. The resulting suspension is has added the aqueous solution (300 ml) containing PLD from ATCC 55717, prepared according to the procedure of example 1 and having an enzymatic activity of 2 U/ml, and added at 10° C. is 1.4 g of calcium chloride, and 1.7 g of sodium acetate trihydrate and glacial acetic acid necessary to obtain a pH of about 4.1. The resulting dipbasic system is heated to a temperature of 25°±2° C. and kept under strong stirring for about 6h. The mixture is then filtered on decalite which is further washed with 2×100 ml of toluene; the organic phase is separated from the aqueous phase, containing the serine excess, and concentrated under reduced pressure to give a residue which is added to 320 ml of n-heptane and 100 ml of methanol. The lower methanol phase is discarded whereas the higher one is diluted with 35 ml of heptane and further extracted with 95 ml of methanol. The higher phase is separated, concentrated under vacuum to small volume and added under stirring at −5° C. with 250 ml of acetone to give, upon filtration and drying under vacuum, 7.3 g of PS(L) calcium salt with a 84% HPLC.

EXAMPLE 5

Preparation of DLPS(L) starting from DLPC.

Repeating the procedure described in example 2, but using 20 g of L-a-dilinoneylphosphatidylcholine, referred to as DLPC, instead of 20 g of Epikuron 200, 15.1 g of L-a-dilinoneylphosphatidyl-L-serine, referred to as DLPS (L), as the calcium salt (96% HPLC purity), are obtained.

EXAMPLE 6

Recovery and recycle of L-serine.

An aqueous solution (10 l), obtained at the end of a transphosphatidylation reaction according to the procedure of example 3, after separation of the toluene solution and filtration on decalite, was treated with 0.3 kg of activated charcoal and the pH was adjusted to 5.7 by adding a 30%

NaOH aqueous solution. The resulting solution was kept for 4 h in a tangential flow electrodialysis apparatus, keeping the pH of the feeding chamber at 5.7±0,5.

Conductivity in the feeding chamber during said time decreased from a starting value of 12,700 µ Siemens/cm to a final value of 480 µ Siemens/cm. The L-serine aqueous solution (97% amino acid recovery), suitably concentrated by reverse osmosis, was used again in place of fresh solid L-serine in a subsequent transphosphatidylation reaction with similar results.

We claim:

1. A process for the preparation of phosphatidylserines compounds of formula (I)

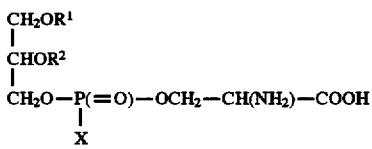

wherein:
$R^1$ and $R^2$, which are the same or different, are a $C_{10}$–$C_{30}$ acyl; X=OH or OM, wherein M is an alkali, alkaline-earth metal, ammonium or alkylammonium; which process comprises reacting phosphatides of general formula (II)

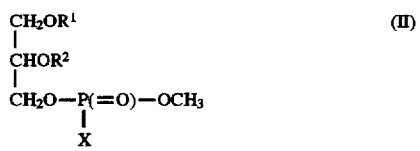

wherein $R^1$, $R^2$ and X have the above defined meanings and $R^3$=$CH_2$—$CH_2NH_2$ or $CH_2$—$CH_2N^+(CH_3)_3$, with racemic or enantiomerically pure serine, in a water/organic solvent diphasic system, in the presence of crude phospholipase D from centrifuged fermentation broths of microorganisms strains producing extracellular PLD having a high transphosphatidylation activity.

2. A process according to claim 1, wherein the organic solvent is toluene.

3. A process according to claim 1, wherein the phosphatides of general formula (II) are mixtures of phosphatidylcholine and/or -ethanolamine of natural origin, selected from soy and egg lecithins, having a phospholipids content ranging from 20% to 95%.

4. A process according to claim 1, wherein the reaction pH ranges from 4 to 4.5.

5. A process according to claim 1, wherein the reaction temperature is 25° C.±5° C.

6. A process according to claim 1, wherein the crude phospholipase D is produced by Streptomyces strain ATCC 55717.

7. A process according to claim 1, wherein the phosphatidylserine is phosphatidyl-(L)-serine and wherein $R^1$ and $R^2$ are acyl chains of palmitic, stearic, oleic, linoleic or linolenic acids in proportions substantially the same as that of soy lecithin.

8. A process according to claim 1, wherein the phosphatidylserine is phosphatidyl-(L)-serine and wherein $R^1$ and $R^2$ are acyl chains of palmitic, stearic, palmitoleic, oleic, linoleic, arachidonic acids in proportions substantially the same as that of egg lecithin.

9. A process according to claim 1, wherein the phosphatidylserines in an alkali, alkaline-earth, ammonium or alkylammonium salts form, are selectively extracted from PS-containing phospholipid mixtures in a dipbasic system of organic solvents.

10. A process according to claim 9, wherein the phosphatidylserine is selectively extracted from a corresponding calcium salt in a heptane/methanol mixture.

11. A process according to claim 10, wherein the phosphatidylserine is crystallized from heptane/acetone, in the form of a calcium salt, and subsequently converted into another salt.

12. A process according to claim 1, wherein the serine is L-serine.

13. The process of claim 10, wherein phospholipids are extracted in a purified form.

14. The process of claim 13, wherein the phospholipids are one or more of PC, PE, PA and corresponding lysophospholipids.

15. The process of claim 1, wherein $R^1$ and $R^2$ are mono- or polyunsaturated acyl.

16. The process of claim 1, wherein M is an inner salt of ammonium or alkylammonium.

* * * * *

UNITED STATES PATENT AND TRADEMARK OFFICE
CERTIFICATE OF CORRECTION

PATENT NO. : 5,700,668
DATED : December 23, 1997
INVENTOR(S) : Lorenzo DE FERRA et al It is certified that error appears in the above-identified patent and that said Letters Patent is hereby corrected as shown below:

At column 1, line 11; column 2, line 15; and column 6, line 37, change "dipbasic" to --diphasic--.

IN THE CLAIMS:

At column 7, line 30, in formula (II) of claim 1, 3rd line of said formula, change "-OCH$_3$" to -- -OR$^3$ --.

At column 8, line 23, in the 4th line of claim 9, change "dipbasic" to --diphasic--.

Signed and Sealed this

Thirteenth Day of July, 1999

Attest:

Attesting Officer

Q. TODD DICKINSON

Acting Commissioner of Patents and Trademarks